United States Patent
Xu et al.

(10) Patent No.: US 11,544,842 B2
(45) Date of Patent: Jan. 3, 2023

(54) MEDICAL IMAGE DIAGNOSTIC APPARATUS, MEDICAL IMAGING APPARATUS AND MEDICAL IMAGING METHOD

(71) Applicant: CANON MEDICAL SYSTEMS CORPORATION, Otawara (JP)

(72) Inventors: Qiqi Xu, Chaoyang (CN); Fanjie Meng, Chaoyang (CN); Hitoshi Yamagata, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 7 days.

(21) Appl. No.: 16/600,693

(22) Filed: Oct. 14, 2019

(65) Prior Publication Data

US 2020/0167912 A1 May 28, 2020

(30) Foreign Application Priority Data

Nov. 23, 2018 (CN) .......................... 201811405328.6

(51) Int. Cl.
*G06T 7/00* (2017.01)
*G06T 7/11* (2017.01)
*G06V 10/40* (2022.01)

(52) U.S. Cl.
CPC .............. *G06T 7/0012* (2013.01); *G06T 7/11* (2017.01); *G06V 10/40* (2022.01); *A61M 2210/0693* (2013.01); *G06T 2207/20128* (2013.01); *G06T 2207/30096* (2013.01)

(58) Field of Classification Search
CPC ................. G06T 7/0012; G06T 7/11; G06T 2207/20128; G06T 2207/30096; G06T 2207/10088; G06T 2207/10081; G06T 7/174; G06T 7/187; G06T 2207/10072; G06T 2200/04; G06T 7/62; G06T 2207/20221; G06T 2207/20104; G06K 9/46; A61M 2210/0693
See application file for complete search history.

(56) References Cited

U.S. PATENT DOCUMENTS

| | | | |
|---|---|---|---|
| 8,190,232 B2 | 5/2012 | Zhang et al. | |
| 2004/0059214 A1* | 3/2004 | Tomoda | A61B 5/055 600/410 |
| 2016/0209995 A1* | 7/2016 | Jeon | G06T 5/003 |
| 2017/0076452 A1* | 3/2017 | Yui | G06T 7/11 |
| 2018/0070903 A1* | 3/2018 | Maeda | G06T 7/0014 |
| 2018/0360408 A1* | 12/2018 | Quan | G16H 50/50 |
| 2020/0175745 A1* | 6/2020 | Wang | A61B 6/03 |

* cited by examiner

*Primary Examiner* — Vu Le
*Assistant Examiner* — Winta Gebreslassie
(74) *Attorney, Agent, or Firm* — Oblon, McClelland, Maier & Neustadt, L.L.P.

(57) ABSTRACT

A medical image diagnostic apparatus according to an embodiment includes processing circuitry. The processing circuitry is configured to obtain image data which is generated by scanning a brain of a subject; select a target region from the image data; extract a connected region of which a brain function is associated with a brain function of the target region, as an additional region; and output scan target region including the target region and the additional region.

14 Claims, 11 Drawing Sheets

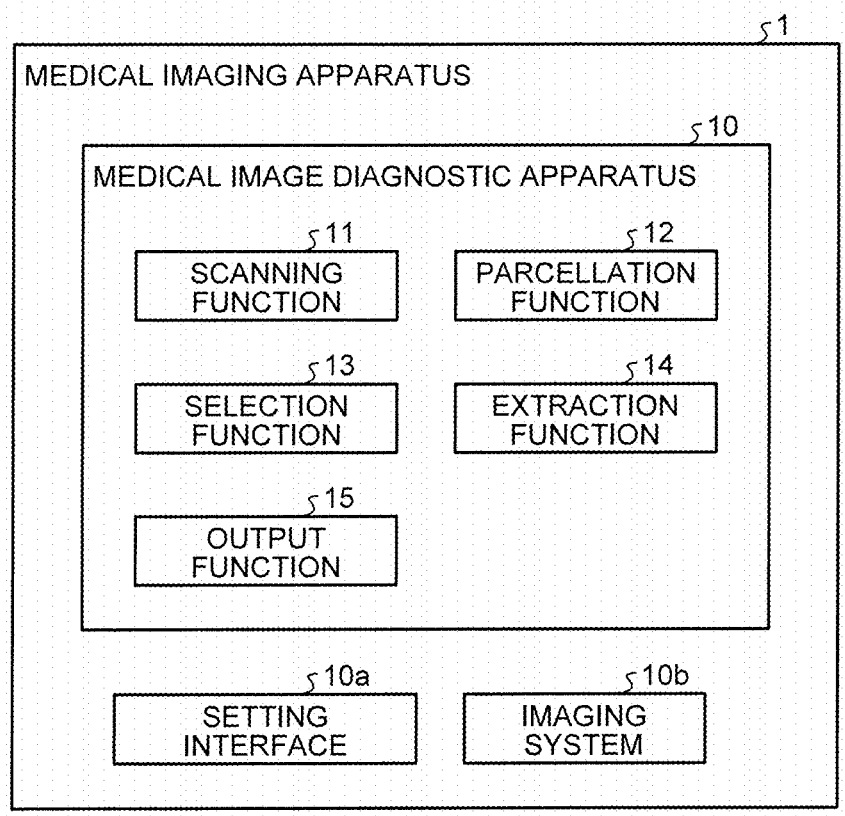

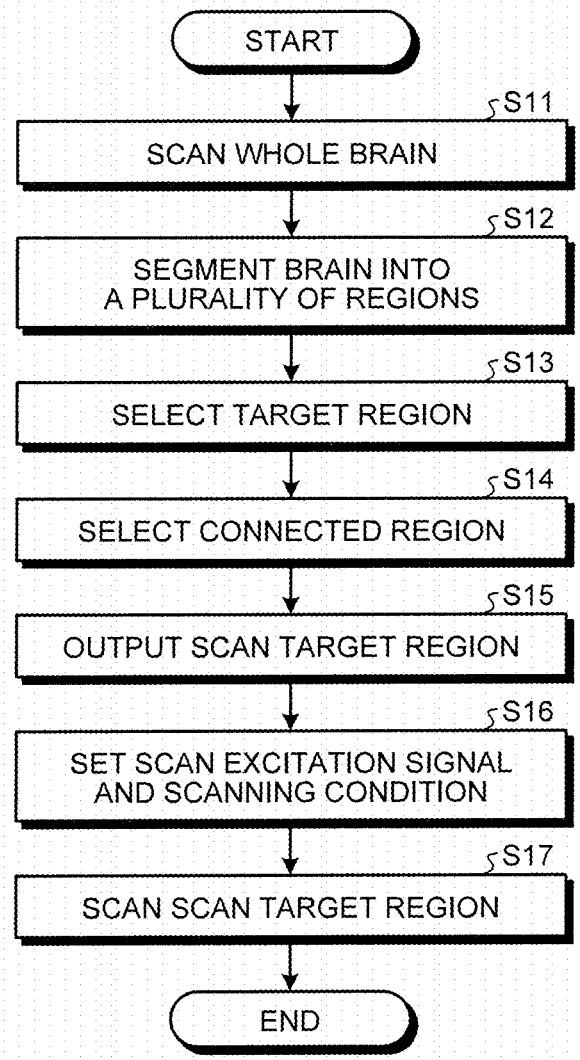

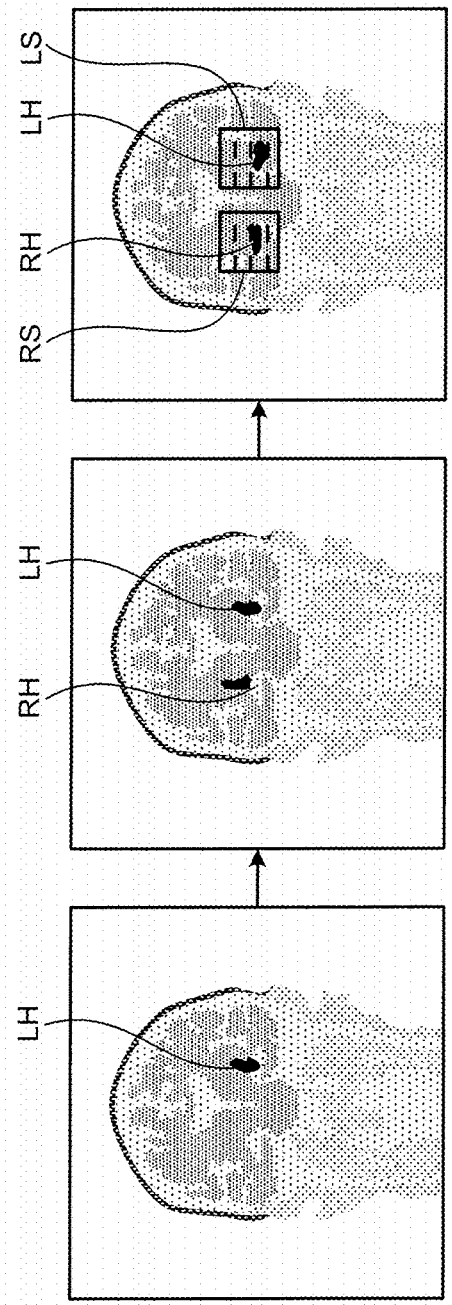

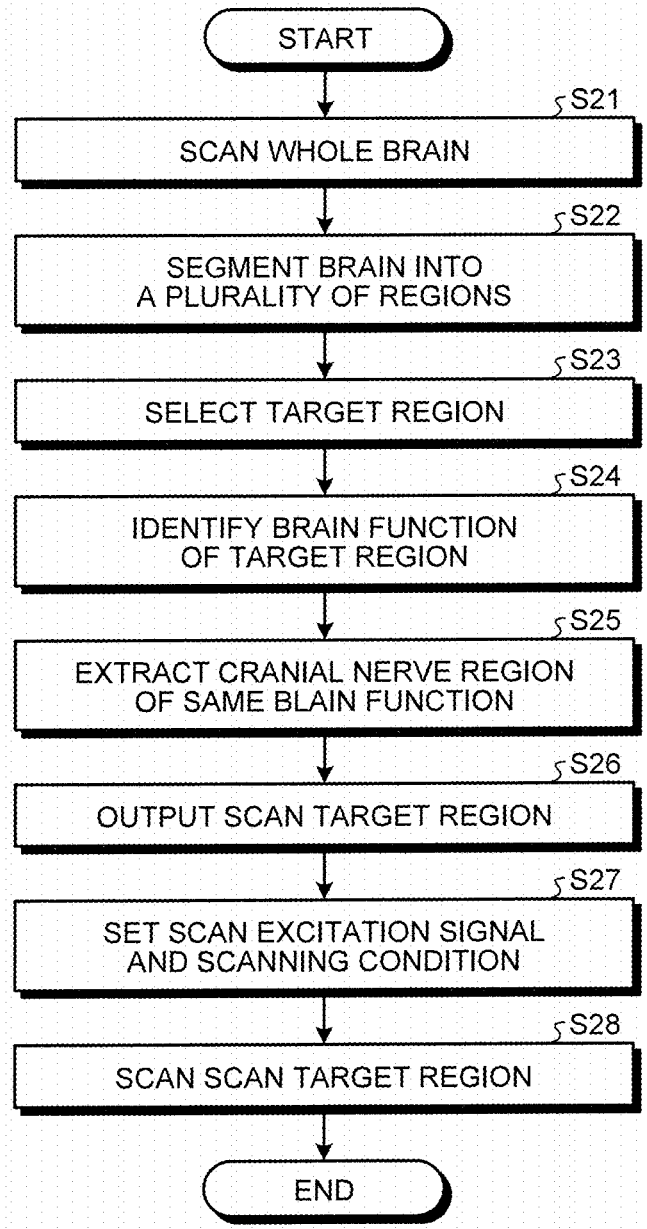

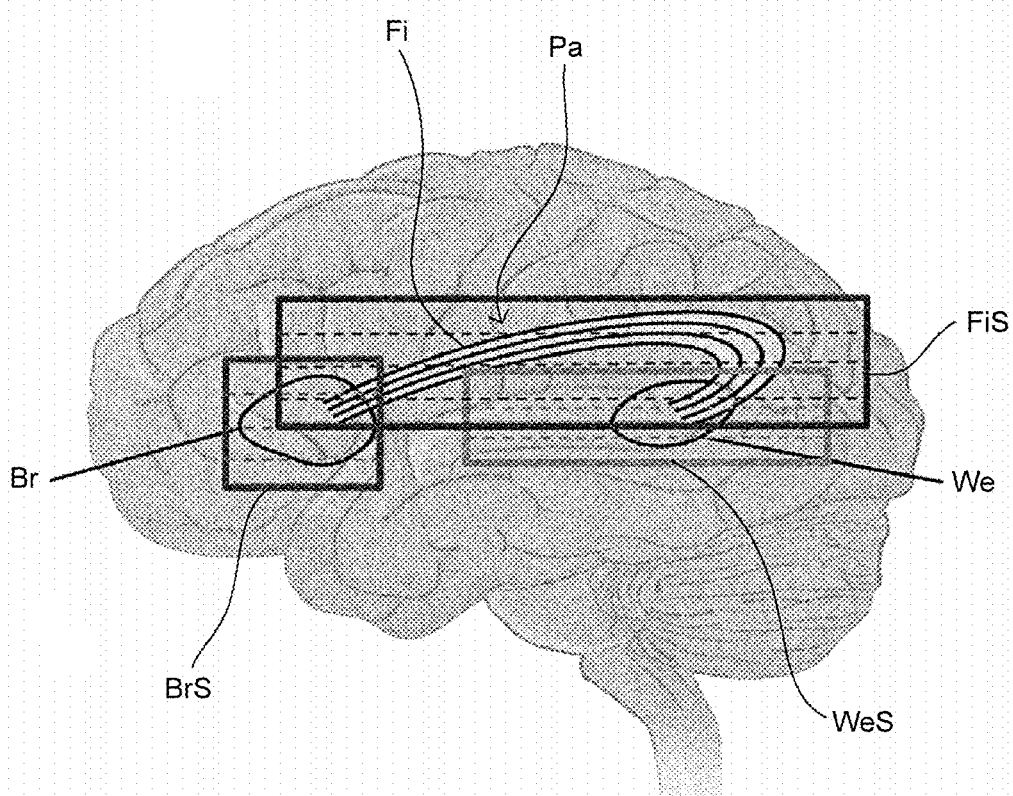

AD

NAME

ENTORHINAL
AMYGDALA
HIPPOCAMPUS

⋮

| NAME | VOLUME (cm³) | PERCENTAGE OF WHOLE BRAIN |
|---|---|---|
| CAUDATE TAIL | 0.14 | 0.007 (-6.46) ↓ |
| CEREBRAL CORTEX | 638.87 | 30.601 (1.13) |
| HIPPOCAMPUS | 7.62 | 0.365 (-1.57) |
| THIRD VENTRICLE | 4.14 | 0.198 (2.37) ↑ |

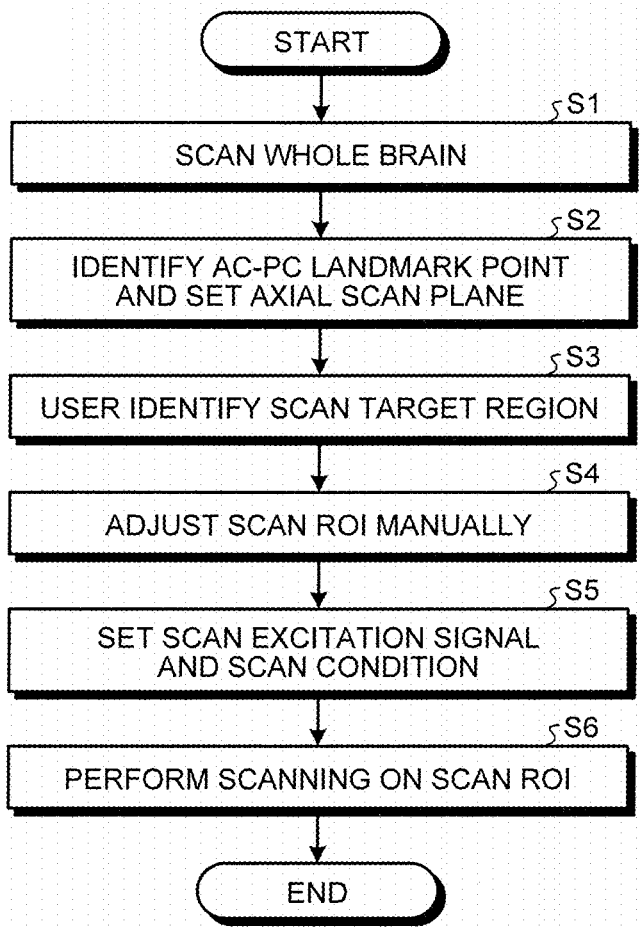

MEDICAL IMAGE DIAGNOSTIC APPARATUS, MEDICAL IMAGING APPARATUS AND MEDICAL IMAGING METHOD

CROSS-REFERENCE TO RELATED APPLICATIONS

This application is based upon and claims the benefit of priority from Chinese Patent Application No. 201811405328.6, filed on Nov. 23, 2018, the entire contents of which are incorporated herein by reference.

FIELD

Embodiments described herein relate generally to a medical image diagnostic apparatus, a medical imaging apparatus and a medical imaging method.

BACKGROUND

Conventionally, when an imaging is performed using a medical image diagnostic apparatus such as a magnetic resonance imaging (MRI) apparatus, a scan target region is set in advance by a user.

BRIEF DESCRIPTION OF THE DRAWINGS

FIG. 1 is a block diagram of a configuration of a medical imaging apparatus according to a first embodiment.

FIG. 3 is a flowchart showing a flow of processing of the medical imaging apparatus according to the first embodiment.

FIG. 4 is a schematic diagram of an example of obtaining a connected region in the right brain based on a brain parcellation region in the left brain, thereby obtaining a scan target region.

FIG. 6 is a schematic diagram of an example of obtaining a scan target region of user interest from brain parcellation data according to the second embodiment.

FIG. 7 is a schematic diagram of an example of obtaining a scan target region for a neural pathway having a language function.

FIG. 12 is a flowchart showing the imaging of the Zonally-magnified scan in prior arts.

DETAILED DESCRIPTION

Figure 2A:
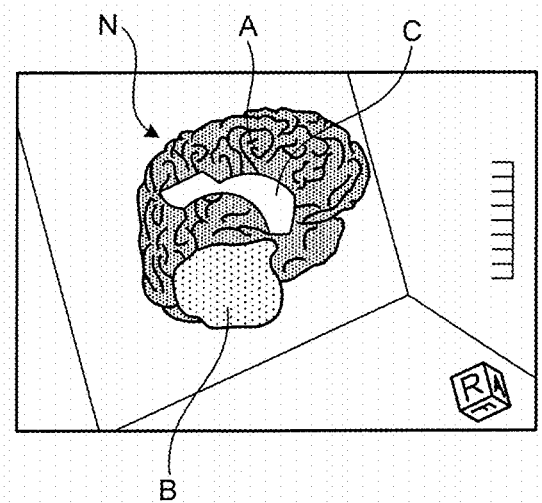
FIGS. 2A-2C are schematic diagrams of an example of obtaining a scan target region of user interest from brain parcellation data according to the first embodiment.

A medical image diagnostic apparatus according to an embodiment includes processing circuitry. The processing circuitry is configured to obtain image data which is generated by scanning a brain of a subject; select a target region from the image data; extract a connected region of which a brain function is associated with a brain function of the target region, as an additional region; and output scan target region including the target region and the additional region.

Exemplary embodiments of a medical image diagnostic apparatus, a medical imaging apparatus and a medical imaging method will be explained in detail below, with reference to the accompanying drawings.

A medical diagnostic apparatus, a medical imaging apparatus and a medical imaging method according to an embodiment set a scan target region of a brain region.

For example, as a method used for imaging a brain region, when performing nuclear magnetic resonance (MR) imaging of the brain, there is an automatic scanning method, the method comprising the steps of: acquiring a three-dimensional positioning image of a brain of a subject; selecting a two-dimensional coronal view and a two-dimensional lateral view from the three-dimensional positioning image; identifying a two-dimensional coronal view and a mid-sagittal plane (MSP) line in a two-dimensional lateral view, and calculating a three-dimensional MSP based on the MSP line; reconstructing the positioning image based on the three-dimensional MSP to obtain an MSP image of the brain of the subject; identifying the crista galli (CG) and the tip of the occipital bone (TOB) in the MSP image of the brain of the subject; calculate a transformation matrix based on the MSP, CG, and TOB as anatomical landmarks in the MSP image, obtain the scanning plan of the subject using the transformation matrix, and output the scanning plan.

In the method of automatically scanning a brain region in Patent Document 1, it is possible to automatically obtain MSP, CG and TOB as anatomical landmarks to perform formal MR imaging. However, when the user wants to scan a small region of the brain to obtain a high-resolution image, it can't be realized by the above scanning method.

With regard to the above situation, there is currently a technique for performing Zonally-magnified scanning on a small region of the brain, such as ZOOM (Zonally-magnified Oblique Multislice)-EPI (Echo Planar Imaging). FIG. 12 shows a flow chart of the Zonally-magnified scanning technique.

In step S1, the whole brain is scanned to obtain volume data of the brain; in step S2, the AC-PC (Anterior Commissure-Posterior Commissure) landmark point is identified in the volume data of the brain, thereby setting an axial scanning plane, according to the axial scanning plane, the scanning device can automatically set the coronal scanning plane and the sagittal scanning plane; in step S3, the user identifies the scanning target region, such as the hippocampus; in step S4, for the identified scanning target region, the scanning region of interest (hereinafter referred to as scanning ROI) including the scanning target region is manually adjusted by the user; in step S5, for the scanning ROI, the scanning excitation signal and the scanning condition including the scanning parameters of the scanning repetition time and the scanning echo time are set by the user or the scanning apparatus; and in step S6, the user scans the scanning ROI using the scanning apparatus.

In the Zonally-magnified scanning technique described above, in step S3 and step S4, since the user identifies a small scanning target region and manually adjusts the scan ROI for the scanning target region, it takes a lot of time and often the scan ROI can't be accurately determined, therefore, the MR image of the scanned ROI cannot be obtained and the diagnosis of the disease cannot be performed.

Therefore, in view of the above, the embodiments provide a medical image diagnostic apparatus, a medical imaging apparatus and a medical imaging method that automatically identifies regions related to a brain functions based on designation of brain parcellation data to output a scan target region.

The medical image diagnostic apparatus according to an embodiment includes processing circuitry configured to obtain image data which is generated by scanning a brain of a subject; select a target region from the image data; extract a connected region of which a brain function is associated with a brain function of the target region, as an additional region; and output a scan target region including the target region and the additional region.

In the medical image diagnostic apparatus according to an embodiment, the processing circuitry is further configured to set one region of the target region and the additional region for one of a right brain and a left brain of the brain of the subject, and set a scan target region including a region corresponding to the one region for the other of the right brain and the left brain for which the one region is not set.

The medical image diagnostic apparatus according to an embodiment further includes a first storage configured to store the scan target region output by the processing circuitry in association with subject identification information for identifying the subject.

The medical image diagnostic apparatus according to an embodiment further includes a second storage configured to store a plurality of lesion patterns and a plurality of regions of the brain, each lesion pattern of the plurality of lesion patterns being associated with at least one region of the plurality of region of the brain, and in the medical image diagnostic apparatus, the processing circuitry is further configured to read, from the second storage, at least one region being associated with a lesion pattern selected by an user from among the plurality of legion patterns, and to select the read region as the scan target region.

In the medical image diagnostic apparatus according to an embodiment, the processing circuitry is further configured to calculate a parameter related to a region of the brain, compare the parameter with a preset parameter range for the region of the brain, and, when the parameter is outside the parameter range, determine the region of the brain as an abnormal region, and select the abnormal region as the target region.

The medical image diagnostic apparatus according to an embodiment further includes a third storage configured to store an atlas including a plurality of regions into which volume data of the brain segmented, and in the medical image diagnostic apparatus, the processing circuitry is further configured to, when a user selects a region from among the plurality of regions included in the atlas, select a region corresponding to the region selected by the user from the regions included in the brain in the image data, and select the region as the target region.

In the medical image diagnostic apparatus according to an embodiment, the connected region is a cranial nerve region.

The medical image diagnostic apparatus according to an embodiment further includes a fourth storage configured to store connection information associating, with respect to each of a plurality of brain functions, a plurality of cranial nerve regions constituting a neural pathway related to a same brain function, and in the medical image diagnostic apparatus, the processing circuitry is further configured to identify the brain function of the target region, and determine, by referring to the connection information, at least one cranial nerve region constituting a neural pathway related to a brain function that is identical to the brain function of the target region, and extract the at least one cranial nerve region from the image data, as the additional region.

The medical imaging apparatus according to an embodiment includes the medical image diagnostic apparatus described above; a setting interface configured to set an excitation signal for exciting the scan target region and a scanning condition with respect to the scan target region; and an imaging system configured to scan the scan target region based on the excitation signal and the scanning condition.

According to an embodiment, when a Zonally-magnified scan is performed on a plurality of small regions of the brain, it is possible to automatically search for a plurality of small regions and set a scan target region thereto, so that it is possible to accurately determine the scan target region without spending a lot of time.

The medical image diagnostic apparatus according to an embodiment is applied to the technique of imaging a brain, and can be applied, for example, to the technique of performing MR imaging on a brain.

Various embodiments of the present application will be described in detail below with reference to the accompanying drawings.

First Embodiment

As shown in FIG. 1, the medical imaging apparatus 1 of the first embodiment includes a medical image diagnostic apparatus 10, a setting interface 10a, and an imaging system 10b, and the medical image diagnostic apparatus 10 includes a scanning function 11, a parcellation function 12, a selection function 13, an extraction function 14 and an output function 15.

The medical imaging diagnostic apparatus 10 includes processing circuitry and memory, and the processing circuitry has the scanning function 11, the parcellation function 12, the selection function 13, the extraction function 14, and the output function 15. For example, the processing circuitry may be realized by a processor. For example, the memory may be realized by a semiconductor memory element such as a Random Access Memory (RAM), a flash memory, or the like, a hard disk, an optical disk, or the like.

The scanning function 11 scans (images) a body part of the subject. In the present embodiment, the brain of the subject (patient or the like) is scanned to generate volume data of the whole brain. The scan can be, for example, a Magnetization Prepared Rapid Acquisition Gradient Echo sequence (MPRAGE) scan.

Generally, in MR imaging, a pre-scan to obtain a locator image (also called localizer image) is performed before a main-scan to obtain a diagnostic image is performed. In the present embodiment, the scan of the whole brain by the scanning function 11 may be performed as a pre-scan to obtain a locator image or as a main-scan to obtain a diagnostic image.

The parcellation function 12 segments the volume data generated by the scanning function 11. In the present embodiment, the volume data of the whole brain generated by the scanning function 11 is segmented into a plurality of blocks, i.e., regions, according to the brain function. As shown in FIG. 2A, it is schematically shown that the volume data (abbreviated as brain data) N of the whole brain is segmented into region A, region B, and region C, but in practice, the brain data N is segmented into dozens or even more than hundreds of regions.

Figure 2B:
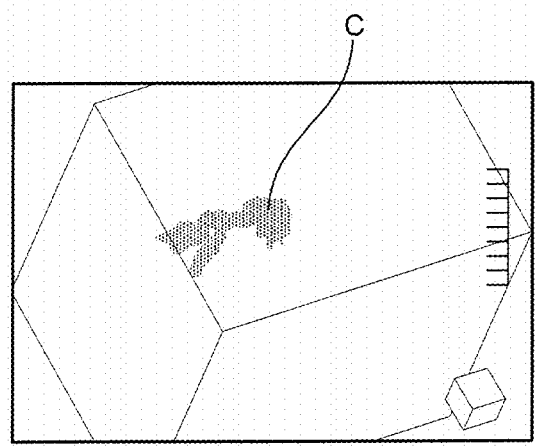

The selection function 13 selects a target region on which a user (doctor or the like) wants to perform Zonally-magnified scan from the plurality of regions segmented by the parcellation function 12. As shown in FIG. 2B, the selection function 13 selects the region C from the plurality of regions segmented by the parcellation function 12.

Figure 2C:
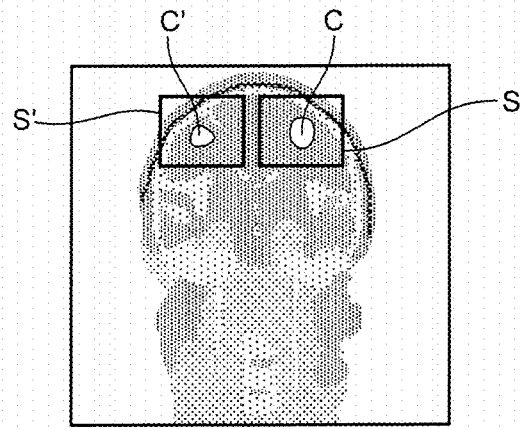

The extraction function 14 extracts a connected region whose brain function is connected with the target region selected by the selection function 13 from the plurality of regions segmented by the parcellation function 12, as an additional region. Here, the brain function connection refers to the connection of brain functions between respective regions of the brain that has the same or similar brain functions, or used to complete a certain action, perform a language expression, recall a memory, and the like. As shown in FIG. 2C, the extraction function 14 extracts the connected region C' whose brain function is associated with the region C, as the additional region.

The output function 15 outputs a region including the region selected by the selection function 13 and the additional region extracted by the extraction function 14 as the scan target region. As shown in FIG. 2C, the output function 15 outputs the scan target region S including the selected region C selected by the selection function 13 and the scan target region S' including the additional region C' extracted by the extraction function 14.

The setting interface 10a sets an excitation signal for exciting the scan target region output by the output function 15 and a scanning condition with respect to the scan target region including the scanning parameters of the scanning repetition time (TR), the scanning echo time (TE), and the like.

The setting interface 10a receives input operations of various types of instructions and various types of information from the operator. More specifically, the setting interface 10a is connected to the processing circuitry of the imaging system 10b, and converts the input operations received from the operator into electrical signals, and outputs the electrical signals to the processing circuitry. For example, the setting interface 10a may be realized by a trackball, a switch button, a mouse, a keyboard, a touch-pad on which an input operation can be performed by touching the operation surface thereof, a touch-screen in which a display screen and a touch-pad are integrally formed, a contactless input circuit using an optical sensor, an audio input circuit, and/or the like that are used for setting an imaging condition, a Region of Interest (ROI), and the like. In the present disclosure, the setting interface 10a does not necessarily have to include one or more physical operational component parts such as a mouse, a keyboard, and/or the like. Examples of the setting interface 10a include, for instance, electrical signal processing circuitry configured to receive an electrical signal corresponding to an input operation from an external input device provided separately from the apparatus and to output the electrical signal to a controlling circuit.

The imaging system 10b scans the scan target region output by the output function 15 based on the excitation signal and the scanning condition set by the setting interface 10a. The imaging is, for example, a Zonally-magnified scan using ZOOM-EPI technology.

For example, the imaging system 10b displays obtained images of the scan target region, i.e., an image of the target region and an image of the additional region on the display side by side. Alternatively, the imaging system 10b may display the image of the target region and the image of the additional region on the display while switching them in accordance with a request from the user.

Although not illustrated in FIG. 1, the imaging system 10b includes a static magnetic field magnet, a gradient coil, a gradient power source, a whole body (WB) coil, transmitter circuitry, a local coil, receiver circuitry, a gantry, a couch, a display, a storage, and processing circuitry.

The static magnetic field magnet is configured to generate a static magnetic field in an imaging space in which a subject is imaged. More specifically, the static magnetic field magnet is formed to have a hollow and substantially circular cylindrical shape (which may have an oval cross-section orthogonal to the central axis thereof) and is configured to generate the static magnetic field in the imaging space positioned inside the circular cylinder. For example, the static magnetic field magnet includes a cooling container formed to have a substantially circular cylindrical shape and a magnet such as a superconductive magnet that is immersed in a cooling member (e.g., liquid helium) filling the cooling container. In this situation, for example, the static magnetic field magnet may be configured to generate the static magnetic field by using a permanent magnet.

The gradient coil is arranged on the inside of the static magnetic field magnet and is configured to generate gradient magnetic fields along a plurality of axial directions, within the imaging space in which the subject is imaged. More specifically, the gradient coil is formed to have a hollow and substantially circular cylindrical shape (which may have an oval cross-section orthogonal to the central axis thereof) and is configured to generate the gradient magnetic fields along the axial directions of X-, Y-, and Z-axes that are orthogonal to one another, within the imaging space positioned inside the circular cylinder. In this situation, the X-axis, the Y-axis, and the Z-axis structure an apparatus coordinate system unique to the medical imaging apparatus 1. For example, the Z-axis coincides with the axis of the circular cylinder of the gradient coil and is set so as to extend along a magnetic flux of the static magnetic field generated by the static magnetic field magnet. Further, the X-axis is set so as to extend in a horizontal direction orthogonal to the Z-axis. The Y-axis is set so as to extend in a vertical direction orthogonal to the Z-axis.

By supplying an electric current to the gradient coil, the gradient power source is configured to cause the gradient magnetic fields to be generated along the axial directions of the X-, Y-, and Z-axes, within the space provided on the inside of the gradient coil. As explained above, as a result of the gradient power source generating the gradient magnetic fields extending along the axial directions of the X-, Y-, and Z-axes, the gradient magnetic fields are generated along a readout direction, a phase-encoding direction, and a slice direction, respectively. The gradient magnetic fields are superimposed on the static magnetic field generated by the static magnetic field magnet and append spatial position information along the respective direction to Magnetic Resonance (MR) signals emitted from the subject.

The WB coil is arranged on the inside of the gradient coil and configured to have a function of a transmitter coil that applies a Radio Frequency (RF) magnetic field to the imaging space in which the subject is imaged and a function of a receiver coil that receives the MR signals emitted from the subject due to an influence of the RF magnetic field. More specifically, the WB coil is formed to have a hollow and substantially circular cylindrical shape (which may have an oval cross-section orthogonal to the central axis thereof) and is configured to apply the RF magnetic field to the imaging space positioned inside the circular cylinder, on the basis of an RF pulse signal supplied thereto from the transmitter circuitry. Further, the WB coil is configured to receive the MR signals emitted from the subject due to the influence of the RF magnetic field and to output the received MR signals to the receiver circuitry.

The transmitter circuitry is configured to output an RF wave signal corresponding to a Larmor frequency to the WB coil. More specifically, the transmitter circuitry includes an oscillator, a phase selector, a frequency converter, an amplitude modulator, and an RF amplifier. The oscillator is configured to generate an RF wave (radio frequency) signal having a resonant frequency (the Larmor frequency) unique to a target atomic nucleus placed in the static magnetic field. The phase selector is configured to select a phase of the RF wave signal. The frequency converter is configured to convert the frequency of the RF wave signal output from the phase selector. The amplitude modulator is configured to generate an RF pulse signal, by modulating the amplitude of the RF wave signal output from the frequency converter, with the waveform of a sinc function, for example. The RF amplifier is configured to power-amplify the RF pulse signal output from the amplitude modulator and to output the result to the WB coil.

The local coil is configured to receive the MR signals emitted from the subject. More specifically, the local coil is attached to the subject placed on the inside of the WB coil and is configured to receive the MR signals emitted from the subject due to the influence of the RF magnetic field applied by the WB coil and to output the received MR signals to the receiver circuitry. For example, the local coil is a receiver coil prepared for any of various sites subject to an imaging process and may be a receiver coil for the head, a receiver coil for the neck, a receiver coil for a shoulder, a receiver coil for the chest, a receiver coil for the abdomen, a receiver coil for a leg, a receiver coil for the spine, or the like. In this situation, the local coil may further have a function of a transmitter coil configured to apply an RF magnetic field to the subject. In that situation, the local coil is connected to the transmitter circuitry and is configured to apply the RF magnetic field to the subject on the basis of an RF pulse signal supplied thereto from the transmitter circuitry.

The receiver circuitry is configured to generate MR signal data on the basis of the MR signals output from either the WB coil or the local coil and to output the generated MR signal data to the processing circuitry. For example, the receiver circuitry includes a selector, a pre-amplifier, a phase detector, and an Analog/Digital (A/D) converter. The selector is configured to selectively receive an input of the MR signals output from either the WB coil or the local coil. The pre-amplifier is configured to power-amplify the MR signals output from the selector. The phase detector is configured to detect the phase of the MR signals output from the pre-amplifier. The A/D converter is configured to generate the MR signal data by converting an analog signal output from the phase detector into a digital signal, and to output the generated MR signal data to the processing circuitry.

The gantry houses therein the static magnetic field magnet, the gradient coil, and the WB coil. More specifically, the gantry has a bore that is hollow and formed to have a circular cylindrical shape. While the static magnetic field magnet, the gradient coil, and the WB coil are arranged so as to surround the bore, the gantry houses these elements therein. In this situation, the space formed on the inside of the bore of the gantry serves as the imaging space in which the subject is placed when an imaging process is performed on the subject.

In the present example, the configuration is explained in which the imaging system 10b has a so-called tunnel-like structure where the static magnetic field magnet, the gradient coil, and the WB coil are each formed to have a substantially circular cylindrical shape; however, possible embodiments are not limited to this example. For instance, the imaging system 10b may have a so-called open structure where a pair of magnets, a pair of gradient coils, and a pair of RF coils are each arranged so as to face each other while the imaging space in which the subject is placed is interposed therebetween.

The couch includes a couchtop on which the subject is placed. When an imaging process is performed on the subject, the couchtop is inserted to the inside of the bore of the gantry. For example, the couch is installed in such a manner that the longitudinal direction thereof extends parallel to the central axis of the static magnetic field magnet.

The display is configured to display various types of information and various types of images. More specifically, the display is connected to the processing circuitry and is configured to convert data of the various types of information and the various types of images sent thereto from the processing circuitry into display-purpose electrical signals and to output the electrical signals. For example, the display may be realized by using a liquid crystal monitor, a Cathode Ray Tube (CRT) monitor, a touch-panel, or the like.

The storage is configured to store therein various types of data such as MR signal data and image data. For example, the storage may be realized by using a semiconductor memory element such as a Random Access Memory (RAM), a flash memory, or the like, a hard disk, an optical disk, or the like.

The processing circuitry has a couch controlling function, a data acquiring function, an image generating function, and a main controlling function. For example, the processing circuitry may be realized by a processor.

The couch controlling function is connected to the couch and is configured to control operations of the couch by outputting a control-purpose electrical signal to the couch. For example, via the setting interface 10a, the couch controlling function is configured to receive an instruction to move the couchtop in a longitudinal direction, an up-and-down direction, or a left-and-right direction from the operator and to operate a moving mechanism for the couchtop included in the couch so as to move the couchtop according to the received instruction.

The data acquiring function is configured to acquire the MR signal data of the subject by driving the gradient power source, the transmitter circuitry, and the receiver circuitry. More specifically, the data acquiring function acquires the MR signal data by executing various types of pulse sequences on the basis of sequence execution data output from the main controlling function. In this situation, the sequence execution data is information defining a pulse sequence indicating a procedure for acquiring the MR signal data. More specifically, the sequence execution data is information that defines: the timing with which the electric current is to be supplied from the gradient power source to the gradient coil and the intensity of the electric current to be supplied; the intensity of the RF pulse signal to be supplied from the transmitter circuitry to the WB coil and the timing with which the RF pulse signal is to be supplied; the detection timing with which the MR signals are to be detected by the receiver circuitry, and the like. Further, as a result of executing any of various types of pulse sequences, the data acquiring function receives the MR signal data from the receiver circuitry and stores the received MR signal data into the storage. In this situation, a set made up of pieces of MR signal data received by the data acquiring function is stored in the storage as data structuring a k-space as a result of being arranged two-dimensionally or three-dimensionally according to the position information appended thereto by the readout gradient magnetic field, the phase-encoding gradient magnetic field, and the slice gradient magnetic field explained above.

The image generating function is configured to generate an image on the basis of the MR signal data stored in the storage. More specifically, the image generating function generates the image by reading the MR signal data stored in the storage by the data acquiring function and further performing a post-processing process, i.e., a reconstructing process (a Fourier transform or the like) on the read MR signal data. Further, the image generating function stores image data of the generated image into the storage.

The main controlling function is configured to exercise overall control of the imaging system 10b by controlling constituent elements of the imaging system 10b. For example, the main controlling function receives an input of an imaging condition from the operator via the setting interface 20a and generates sequence execution data on the basis of the received imaging condition. The main controlling function then transmits the generated sequence execution data to the data acquiring function and thereby executes various types of pulse sequences. Further, for example, the main controlling function reads image data from the storage in response to a request from the operator and outputs the read image data to the display.

For example, when the processing circuitries of the medical image diagnostic apparatus 10 and the imaging system 10b are each realized by a processor, the processing function of each of the processing circuitries is stored in the storage in the form of a computer-executable program. Further, the processing circuitries realize the functions corresponding to the programs by reading and executing the programs from the storage. In other words, each of the processing circuitries that has read the corresponding program has the function illustrated in the processing circuitry in FIG. 1. In this situation, the example is explained in which the plurality of processors realize the processing functions; however, another arrangement is also acceptable in which the processing circuitries are structured by using a single processor so that the processor realizes the functions by executing the programs. Further, the processing functions of the processing circuitries may be realized as being distributed to a plurality of processing circuitries or as being integrated together into a single processing circuitry, as appropriate. Further, in the above description, the example is explained in which the single storage (i.e., the storage) is configured to store therein the programs corresponding to the processing functions; however, another arrangement is also acceptable in which a plurality of storages are provided in a distributed manner, so that the processing circuitries each read a corresponding one of the programs from a corresponding one of the individual storages.

In the following, the work flow of the medical image diagnostic apparatus 10 and the like according to the present embodiment will be described with reference to FIGS. 2 and 3.

As shown in FIG. 3, in step S11, the scanning function 11 scans the brain of the subject to generate volume data of the whole brain. This process at step S11 is realized, for example, as a result of the processing circuitry reading and executing the predetermined program corresponding to the scanning function 11 from the storage.

In step S12, the parcellation function 12 segments the volume data generated by the scanning function 11 into a plurality of regions, for example, region A, region B, region C in FIG. 2A, and the like. This process at step S12 is realized, for example, as a result of the processing circuitry reading and executing the predetermined program corresponding to the parcellation function 12 from the storage.

In step S13, according to the diagnosis request of the user, the selection function 13 selects a target region from a plurality of regions segmented by the parcellation function 12, for example, as shown in FIG. 2B, it selects region C from region A, region B, region C, and the like as the target region. This process at step S13 is realized, for example, as a result of the processing circuitry reading and executing the predetermined program corresponding to the selection function 13 from the storage.

In step S14, the extraction function 14 extracts, as an additional region, an connected region whose brain function is connected with the target region selected by the selection function 13 from the plurality of regions segmented by the parcellation function 12, for example, as shown in FIG. 2C, the brain region whose brain function is the same as that of the region C is selected by the selection function 13, i.e., the connected region C', as the additional region. This process at step S14 is realized, for example, as a result of the processing circuitry reading and executing the predetermined program corresponding to the extraction function 14 from the storage.

In step S15, the output function 15 outputs a region including the region selected by the selection function 13 and the additional region extracted by the extraction function 14 as a scan target region, as shown in FIG. 2C, the output function 15 outputs the scan target region S including the selected region C selected by the selection function 13 and the scan target region S' including the additional region extracted by the extraction function 14. This process at step S15 is realized, for example, as a result of the processing circuitry reading and executing the predetermined program corresponding to the output function 15 from the storage.

In step S16, the setting interface 10a sets an excitation signal for exciting the scan target region output by the output function 15 and a scanning condition with respect to the scan target region including the scanning parameters, as in the example of FIGS. 2A-2C, an excitation signal for exciting the scan target region S and the scan target region S' and scan conditions with respect to the scan target region S and the scan target region S' are output.

In step S17, the imaging system 10b scans the scan target region output by the output function 15 based on the excitation signal and the scanning condition set by the setting interface 10a, as in the example of FIGS. 2A-2C, the imaging system 10b scans the scan target region S and the scan target region S' output by the output function 15.

In the following, other functions of the output function 15 of the present embodiment will be described with reference to FIG. 4.

FIG. 4 shows a coronal plane of the brain, and the three figures on the left, the middle and the right in FIG. 4 are referred to as the left figure, the middle figure and the right figure, respectively. The left figure shows the left hippocampus LH located in the left brain of the brain. The middle figure shows the right hippocampal region RH located in the right brain of the brain and the left hippocampus LH located in the left brain of the brain. The right figure shows the example when the scan target region is set for the right hippocampus RH and the left hippocampus LH.

When the selection function 13 selects the left hippocampus LH (left image) in the left brain as the target region from the plurality of regions segmented by the parcellation function 12, for the other side of the brain (right brain) corresponding the side of the brain (left brain) in which the left hippocampus LH is set, the output function 15 outputs the right hippocampus RH corresponding to the left hippocampus LH (the middle figure), and while setting the region containing the left hippocampus LH as the scan target region LS, also sets the region containing the right hippocampus RH corresponding to the left hippocampus LH as the scan target region RS (the right figure).

Further, it can also be formed that, when the extraction function 14 extracts the left hippocampus LH (left image) in the left brain as the additional region from the plurality of regions segmented by the parcellation function 12, for the other side of the brain, i.e., the right brain, the output function 15 outputs the right hippocampus RH corresponding to the left hippocampus LH (the middle figure), and while setting the region containing the left hippocampus LH as the scan target region LS, also sets the region containing the right hippocampus RH corresponding to the left hippocampus LH as the scan target region RS (the right figure).

As described above, when the selection function 13 selects the target region from the plurality of regions segmented by the parcellation function 12, the extraction function 14 can also automatically extract the connected region whose brain function is connected with the target region from the plurality of regions segmented by the parcellation function 12, and the region output containing the target region and the connection region is automatically set by the output function 15 as the scan target region. Therefore, when performing Zonally-magnified scanning on a plurality of small regions of the brain, the user does not need to manually search respective small regions and set the scan target region for it. Therefore, it is possible to determine the scan target region accurately without spending much time, thereby enabling MR imaging of the scan target region for disease diagnosis.

Second Embodiment

Figure 5:
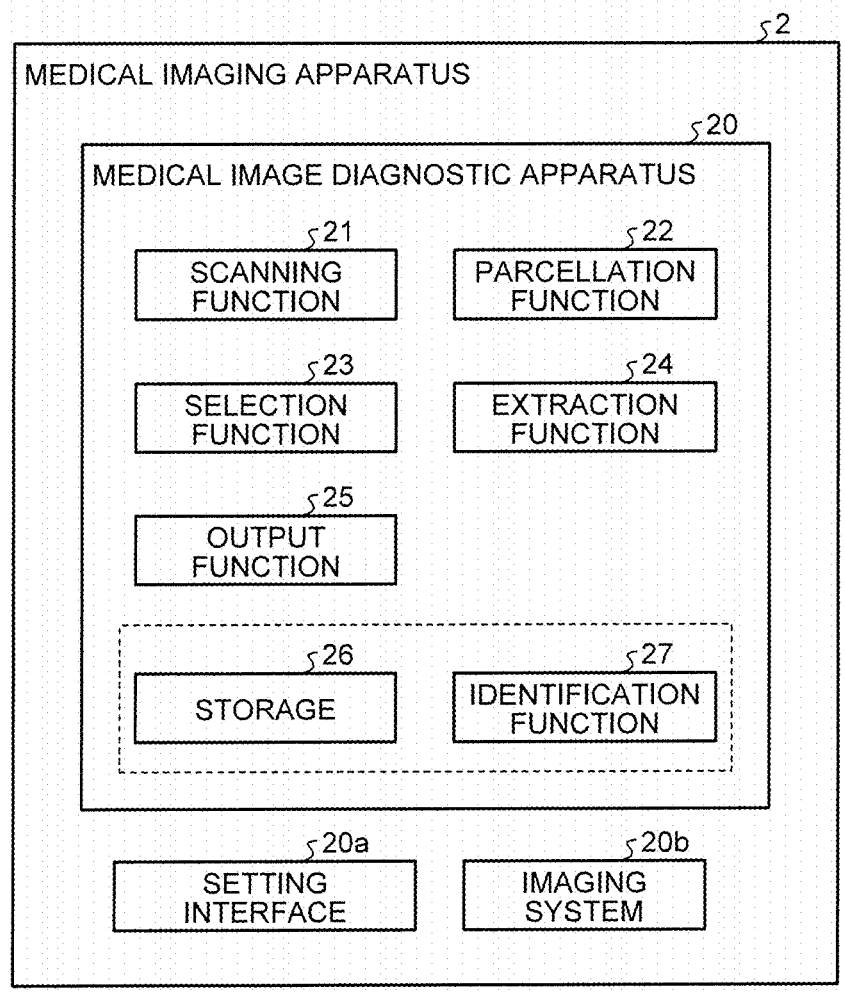
FIG. 5 is a block diagram of the configuration of a medical imaging apparatus involved in a second embodiment.

As shown in FIG. 5, the medical imaging apparatus 2 of the present embodiment includes a medical image diagnostic apparatus 20, a setting interface 20a, and an imaging system 10b, wherein the medical image diagnostic apparatus 20 comprising a scanning function 21, a parcellation function 22, a selection function 23, an extraction function 24 and an output function 25.

The functions of the scanning function 21, the parcellation function 22, the selection function 23, and the output function 25 in the present embodiment are the same as or similar to those of the scanning function 11, the parcellation function 12, the selection function 13, and the output function 15 in the first embodiment, and therefore, it is described in brief. In addition, other parts that are the same as or similar to those of the first embodiment will also be described in brief.

The scanning function 21 is for scanning (capturing) a body part of the subject, and in the present embodiment, the brain of the subject is scanned to generate volume data of the whole brain. The scan can be, for example, a Magnetization Prepared Rapid Acquisition Gradient Echo sequence (MPRAGE) scan.

The parcellation function 22 segments the volume data generated by the scanning function 21. In the present embodiment, the volume data of the whole brain generated by the scanning function 21 is segmented into a plurality of blocks, i.e., regions, according to the brain function.

The selection function 23 selects a target region on which a user wants to perform Zonally-magnified scan from the plurality of regions segmented by the parcellation function 22.

The extraction function 24 extracts a brain neural region whose brain function is connected with the target region selected by the selection function 23. Here, the brain function connection refers to the connection of brain functions between respective regions of the brain that has the same or similar brain function, or used to complete a certain action, perform a language expression, recall a memory, and the like.

The output function 25 outputs a region including the target region selected by the selection function 23 and the additional region extracted by the extraction function 24 as the scan target region.

The setting interface 20a sets an excitation signal for exciting the scan target region output by the output function 25 and a scanning condition with respect to the scan target region including the scanning parameters of the scanning repetition time, the scanning echo time, and the like.

The imaging system 20b scans the scan target region output by the output function 25 based on the excitation signal and the scanning condition set by the setting interface 20a. The imaging is, for example, a Zonally-magnified scan using ZOOM-EPI technology.

In addition, the medical image diagnostic apparatus 20 may further include a storage 26 and an identification function 27 (as shown in the dotted box).

The storage 26 stores connection information that connects the plurality of cranial nerve regions constituting the neural pathway related to the brain function such as language and memory.

The identification function 27 identifies the brain function of the target region selected by the selection function 23.

The extraction function 24 refers to the connection information, and extracts, from the plurality of regions segmented by the parcellation function 12, a plurality of regions of the neural pathway having the same brain function as the target region identified by the identification function 27, that is, the cranial nerve region, as the additional region.

In the following, the work flow of the medical image diagnostic apparatus 20 or the like according to the present embodiment will be described with reference to FIGS. 6 and 7.

In FIG. 7, a neural pathway Pa having a language function is shown, the neural pathway Pa includes a Wernicke's region We, a Broca's region Br, and a nerve connecting fiber Fi connecting the two regions. The connection information that connects the Winik region We and the Broca region Br constituting the neural pathway Pa related to the language function is stored in the storage 26.

As shown in FIG. 6, in step S21, the scanning function 21 scans the brain of the subject to generate volume data of the whole brain. This process at step S21 is realized, for example, as a result of the processing circuitry reading and executing the predetermined program corresponding to the scanning function 21 from the storage.

In step S22, the parcellation function 22 segments the volume data generated by the scanning function 21 into a plurality of regions. This process at step S22 is realized, for example, as a result of the processing circuitry reading and executing the predetermined program corresponding to the parcellation function 22 from the storage.

In step S23, according to the diagnosis request of the user, the selection function 23 selects the target region from a plurality of regions segmented by the parcellation function 22. This process at step S23 is realized, for example, as a result of the processing circuitry reading and executing the predetermined program corresponding to the selection function 23 from the storage.

In step S24, the identification function 27 identifies the brain function of the target region selected by the selection function 23. As shown in FIG. 7, when the target region selected by the selection function 23 is the Winik region We, the identification function 27 identifies that the brain function connected with the Winik region We is the language function. This process at step S24 is realized, for example, as a result of the processing circuitry reading and executing the predetermined program corresponding to the identification function 27 from the storage.

In step S25, the extraction function 24, by referring to the connection information stored in the storage 26, extracts, from the plurality of regions segmented by the parcellation function 12, cranial nerve region of the neural pathway having the same brain function as that of the target region identified by the identification function 27, as the additional region. As shown in FIG. 7, the extraction function 24, by referring to the connection information that connects the Winik region We and the Broca region Br related to the language function, extracts a region whose brain function is the same as the brain function of the Wenikil region We from the plurality of segmented regions, that is, both the Broca region Br with the language function, as the additional region.

In step S26, the output function 25 outputs a region including the region selected by the selection function 23 and the additional region extracted by the extraction function 24 as a scan target region, as shown in FIG. 7, the output function 25 outputs the scan target region WeS including the selected Winik region We selected by the selection function 23 and the scan target region S' including the additional region (i.e., the Broca region Br) extracted by the extraction function 24. Of course, as shown in FIG. 7, in addition to the above-described scan target region, the output function 25 may output a scan target region FiS containing the nerve contact fiber Fi.

In step S27, the setting interface 20a sets an excitation signal for exciting the scan target region output by the output function 25 and a scanning condition with respect to the scan target region including the scanning parameters, as in the example of FIG. 7, an excitation signal for exciting the scan target region WeS and the scan target region BrS as well as the scanning condition with respect to the scan target region WeS and the scan target region BrS is output.

In step S28, the imaging system 20b scans the scan target region output by the output function 25 based on the excitation signal and the scanning condition set by the setting interface 20a, as in the example of FIG. 7, the imaging system 20b scans the scan target region WeS and the scan target region BrS output by the output function 25.

Further, in case the medical image diagnostic apparatus 20 does not have the storage 26 and the identification function 27, the extraction function 24 directly extracts an cranial nerve region whose brain function is associated with the target region selected by the selection function 13 from the plurality of regions segmented by the parcellation function 12 as the additional region, thereby replacing step S24 and step S25 described above.

In the following, a neural pathway involving transient memory and long-term memory, that is, memory brain function, will be described using FIGS. 8A-8C.

Figure 8A:
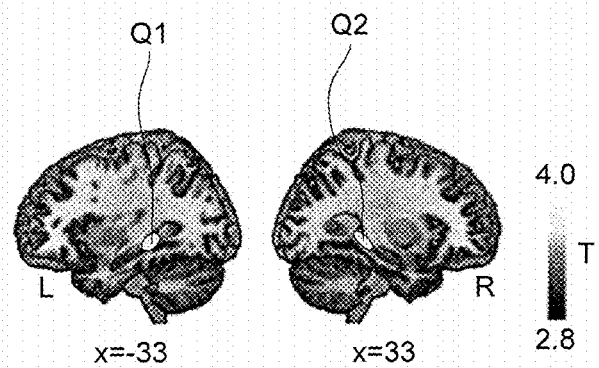
FIGS. 8A-8C are a plot for illustrating a neural pathway having a memory function.
Figure 8B:
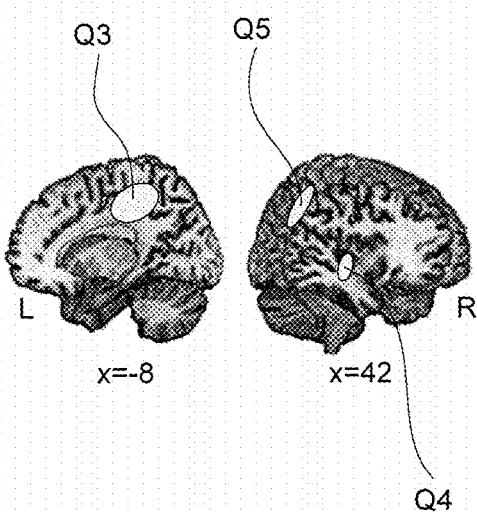
Figure 8C:
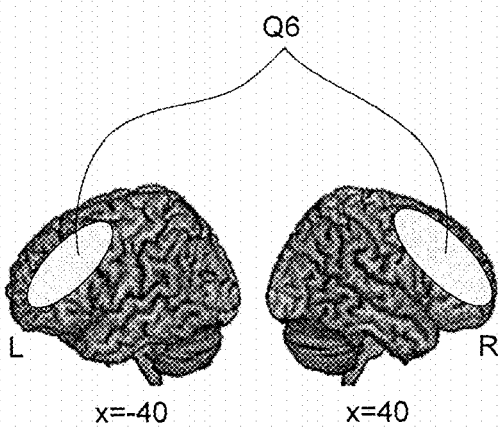

The left hippocampus Q1 is schematically shown in the left figure of FIG. 8A, and the right hippocampus Q2 is shown in the right figure, the posterior cingulate cortex (PCC) Q3 is schematically shown in the left figure of FIG. 8B, and the right middle temporal gyrus (MTG) Q4 and the right lateral parietal cortex (LPC) Q5 are schematically shown in the right figure, and the dorsolateral prefrontal lobe (DLPFC) Q6 is schematically shown in FIG. 8C, these regions, namely, the left hippocampus Q1, the right hippocampus Q2, posterior cingulate cortex Q3, the right middle temporal gyrus Q4, the right lateral parietal cortex Q5 and the dorsolateral prefrontal lobe Q6 is a cranial nerve region related to the brain function of memory which is segmented by the parcellation function 12, and they constitute a neural pathway related to the brain function of memory.

In the medical image diagnostic apparatus 20 of the present embodiment, when the selection function 23 selects any target region in the plurality of regions shown in FIGS. 8A-8C from among the plurality of regions segmented by the parcellation function 22, the extraction function 24 extracts other regions in the plurality of regions shown in FIGS. 8A-8C associated with the brain function from a plurality of regions segmented by the parcellation function 22. For example, when the selection function 23 selects the left hippocampus Q1 as the target region, the extraction function 24 extracts the right hippocampal Q2, the posterior cingulate cortex Q3, the right middle temporal gyrus Q4, the right lateral parietal cortex Q5, and the dorsolateral prefrontal cortex Q6 which has a brain function of memory (i.e. associated with brain function), as the additional regions. Thereafter, the output function 25 outputs the scan target region and the additional region for these target regions.

As described above, when the selection function 23 selects the target region from the plurality of regions segmented by the parcellation function 22, the extraction function 24 can also automatically extract the cranial nerve region whose brain function is connected with the target region, and the output function 25 automatically outputs the target region and the cranial nerve region as the scan target region. Therefore, when performing Zonally-magnified scanning on a plurality of small regions of the brain, the user does not need to manually search respective small regions and set the scan target region for it. Therefore, it is possible to determine the scan target region accurately without spending much time, thereby enabling MR imaging of the scan target region for disease diagnosis.

Further, in the first embodiment, the medical image diagnostic apparatus 10 may further include a storage that associates the scan target region output by the output function 15 and the subject identification information for identifying the subject (such as the name, ID, or identity number and the like of the subject) for storage. Therefore, when the same subject is examined, when the subject identification information such as the name, ID, or identity number is input, the medical image diagnostic apparatus 10 can extract the scan target region when the subject was previously imaged from the storage, and perform imaging for the scan target region, so as to facilitate the user to compare the image captured in the previous examination with the image captured in the current examination, thereby acknowledging the change of the condition of the subject.

Similarly, in the second embodiment, the storage 26 of the medical image diagnostic apparatus 20 may also associate the scan target region output by the output function 25 and the subject identification information for identifying the subject (such as the name, ID, or identity number and the like of the subject) for storage. The same effects as those of the first embodiment described above can be achieved.

Further, in the first embodiment, the medical image diagnostic apparatus 10 may further comprising a storage for storing the lesion pattern in association with the relevant region in the plurality of regions segmented by the parcellation function 12. By the user selecting a certain one of the plurality of lesion patterns, the selection function 13 reads a relevant region corresponding to the selected lesion pattern from the storage, and uses the relevant region as the target region. Further, the extraction function 14 extracts a connection region whose brain function is associated with the target region, and the output function outputs the scan target region.

Figures 9, 10:
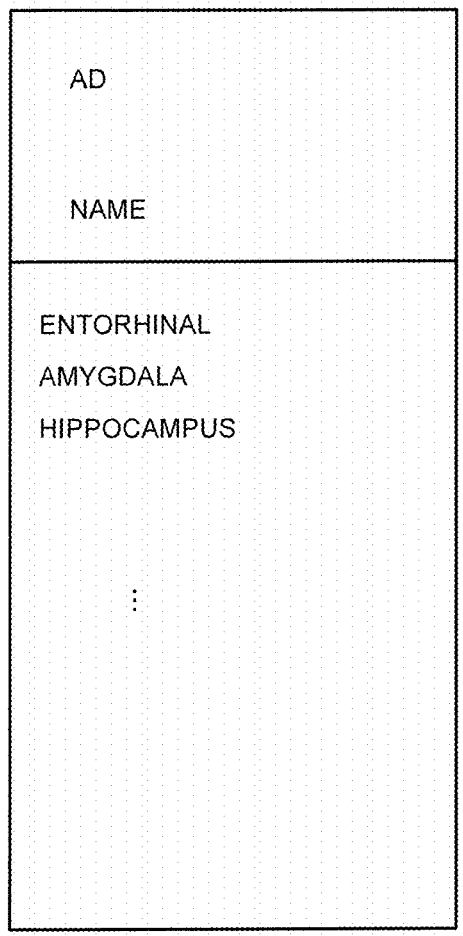
FIG. 9 is a plot showing an example of a region related to Alzheimer disease.
FIG. 10 is an illustration of an example of determining an abnormality of a brain parcellation region.

For example, in FIG. 9, the storage stores Alzheimer's disease (AD) in association with related regions such as the entorhinal area, the amygdala, and the hippocampus. When the selection function 13 selects Alzheimer's disease (AD) by the user, the relevant regions corresponding to the selected lesion pattern of Alzheimer's disease (AD), i.e., the olfactory, the amygdala, and the hippocampus, etc. are read from the storage, and these regions are used as the target region.

Thereby, when the user selects the lesion pattern, the relevant region related to the lesion pattern, that is, the target region, can be obtained. Therefore, the user does not need to select the region segmented in the volume data of the brain, thereby saving time for the user to select the target region, making the imaging easier.

Similarly, in the second embodiment, the storage 26 of the medical image diagnostic apparatus 20 may also store the lesion pattern in association with the relevant region in the plurality of regions segmented by the parcellation function 22. By the user selecting a certain one of the plurality of lesion patterns, the selection function 23 reads a relevant region corresponding to the selected lesion pattern from the storage 26, and uses the relevant region as the target region. The same effects as those of the first embodiment described above can be achieved.

Further, in the first embodiment, the medical image diagnostic apparatus 10 may further comprising a calculation function and a comparison function, the calculation function calculates the volume of the plurality of blocks of the volume data of the whole brain segmented by the parcellation function 12, and further calculates the percentage of the volume of each block with respect to the volume of the whole brain, the comparison function compares the percentage of the volume of each block (the first percentage) calculated by the calculation function with the standard percentage (the second percentage) of each corresponding each preset block with respect to the whole brain of the volume, and calculates the variation of the first percentage with respect to the second percentage, and the calculated variation is compared with the preset range of the volume variation of the block. If the calculated variation exceeds the range of the volume variation, it is determined that the block (region) is abnormal. The selection function 13 selects a block (region) in which an abnormality exists from the plurality of blocks segmented by the parcellation function 12 as a target region. Further, the extraction function 14 extracts a connection region whose brain function is connected with the target region, and the output function outputs the scan target region.

For example, in FIG. 10, it is exemplary shown that the calculation function calculates the volume of the caudate tail, the cerebral cortex, the hippocampus and the third ventricle and the percentage of the respective regions occupying the whole brain, and shows the variation in the percentage of each region with respect to the standard percentage obtained by the comparison function, that is, the value in parentheses, thereby showing the variation in the caudate tail and the variation in the third ventricle exceeds the preset range of the volume variation and the downward arrow in the figure indicates that the volume is too small, and the upward arrow indicates that the volume is too large. Therefore, in FIG. 10, the selection function 13 selects the caudate tail and the third ventricle as the target region.

The region where the volume is abnormal is shown in FIG. 10, and of course, it may be a region where the size, the position, the image greyscale, the magnetic resonance signal, and the like, is abnormal.

Thereby, when the volume data of the whole brain is segmented into a plurality of regions by the parcellation function 12, the target region in which the abnormality exists can be obtained by the calculation function and the comparison function, and therefore, the user does not need to select the region segmented in the volume data of the brain, thereby saving time for the user to select the target region, making the imaging easier.

Similarly, in the second embodiment, the medical image diagnostic apparatus 20 may include the above-described calculation function and the comparison function, and the same effects as those of the first embodiment described above can be achieved.

Further, the medical image diagnostic apparatus 10 may further comprising a storage in which an atlas of a region in which volume data of the brain is segmented is stored in advance, and when the user selects a region after brain parcellation from the atlas, the selection function 13 automatically selects the corresponding region from among the plurality of regions into which the brain of the subject is segmented by the parcellation function 12 as the target region. Further, the extraction function 14 extracts a connection region whose brain function is connected with the target region, and the output function outputs the scan target region.

Figure 11:
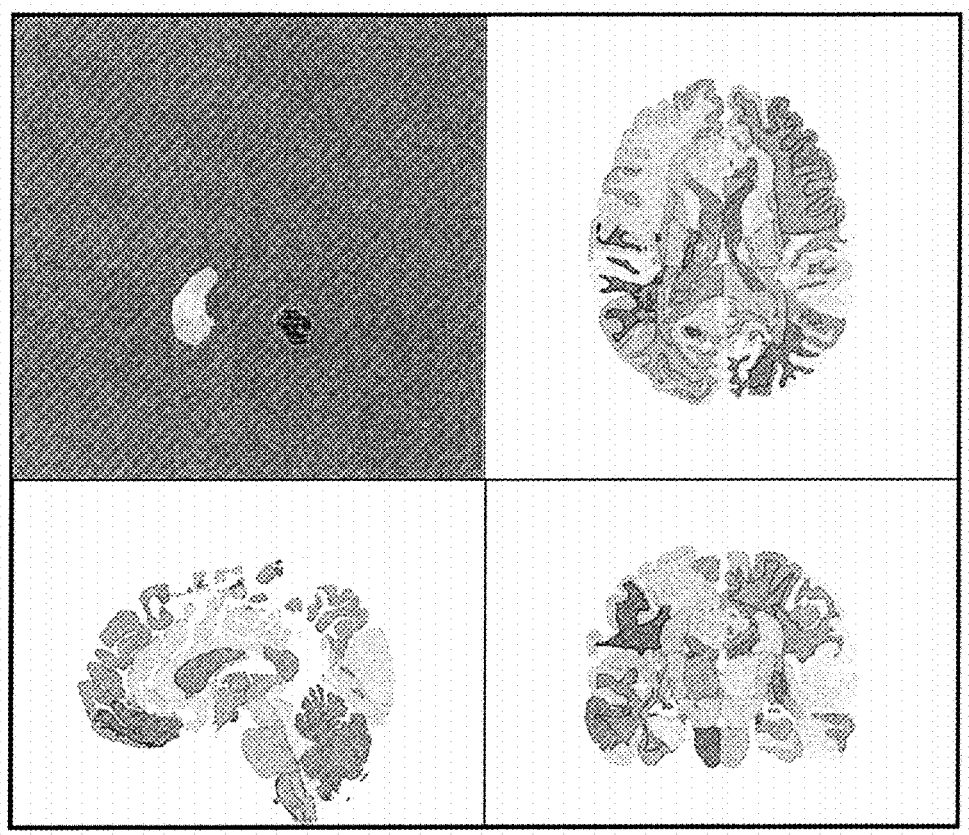
FIG. 11 is a plot showing an example of an atlas of a brain parcellation region and a region obtained from the atlas.

For example, in FIG. 11, the upper right diagram, the lower right diagram, and the lower left diagram respectively shows the axial plane, the coronal plane, and the sagittal plane of the brain pre-stored by the storage, and the upper left diagram shows the brain parcellated blocks (regions) selected from the atlas of the above-described respective planes. That is, when the user selects two blocks (regions) shown in the upper left diagram from the atlas of the respective planes described above, the selection function 13 automatically selects a corresponding one of the plurality of regions segmented by the parcellation function 12 as the target region.

Thereby, when the user selects a region of concern from the above-described atlas, the selection function 13 can automatically select a corresponding region from the brain parcellation region of the subject as the target region, and therefore, the user does not need to select the region segmented in the volume data of the brain, thereby saving time for the user to select the target region, making the imaging easier.

Similarly, in the second embodiment, the storage 26 of the medical image diagnostic apparatus 20 may also pre-store an atlas in which the brain is segmented, and when the user selects a brain parcellation region from the atlas, the selection function 13 automatically selects the corresponding region from the plurality of brain parcellation regions of the subject segmented by the parcellation function 12 as the target region. Further, the extraction function 24 extracts a cranial nerve region whose brain function is connected with the target region, and the output function outputs the scan target region. The same effects as those of the first embodiment described above can be achieved.

The term "processor" used in the explanations of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in a storage, it is also acceptable to directly incorporate the programs in the circuits of the processors. In that situation, the processors realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof.

In this situation, the programs executed by the one or more processors are provided as being incorporated, in advance, in a Read-Only Memory (ROM), a storage, or the like. Alternatively, the programs may be provided as being recorded on a computer-readable storage medium such as a Compact Disk Read-Only Memory (CD-ROM), a flexible disk (FD), a Compact Disk Recordable (CD-R), a Digital Versatile Disk (DVD), or the like, in a file in such a format that is either installable or executable for the devices. Further, the programs may be stored in a computer connected to a network such as the Internet, so as to be provided or distributed as being downloaded via the network. For example, each of the programs is structured with a module including the functions described above. In the actual hardware, as a result of a CPU reading and executing the programs from a storage medium such as a ROM, the modules are loaded into a main storage device so as to be generated in the main storage device.

According to at least one aspect of the embodiments described above, it is possible to easily set the scan target region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising: processing circuitry configured to obtain image data which is generated by scanning a brain of a subject; select a target region from the image data; extract a connected region of which a brain function is associated with a brain function of the target region, as an additional region, wherein the connected region is a cranial nerve region; and set a first scan target region including the target region to scan the target region in the brain, and set a second scan target region including the additional region to scan the additional region in the brain and a first storage configured to store connection information associating, with respect to each of a plurality of brain functions, a plurality of cranial nerve regions constituting a neural pathway related to a same brain function, wherein the processing circuitry is further configured to identify the brain function of the target region, determine, by referring to the connection information, at least one cranial nerve region constituting a neural pathway related to a brain function that is identical to the brain function of the target region, and extract the at least one cranial nerve region from the image data, as the additional region.

2. The medical image diagnostic apparatus according to claim 1, wherein the processing circuitry is further configured to set one region of the target region and the additional region for one of a right brain and a left brain of the brain of the subject, and set a third target region including a region corresponding to the one region for the other of the right brain and the left brain for which the one region is not set.

3. The medical image diagnostic apparatus according to claim 1, further comprising a second storage configured to store the first scan target region and the second scan target region set by the processing circuitry in association with subject identification information for identifying the subject.

4. The medical image diagnostic apparatus according to claim 1, further comprising a third storage configured to store a plurality of lesion patterns and a plurality of regions of the brain, each lesion pattern of the plurality of lesion patterns being associated with at least one region of the plurality of region of the brain, wherein the processing circuitry is further configured to read, from the third storage, at least one region being associated with a lesion pattern selected by a user from among the plurality of lesion patterns, and to select the read region as the target region.

5. The medical image diagnostic apparatus according to claim 1, wherein the processing circuitry is further configured to calculate a parameter related to a region of the brain, compare the parameter with a preset parameter range for the region of the brain, and when the parameter is outside the parameter range, determine the region of the brain as an abnormal region, and select the abnormal region as the target region.

6. The medical image diagnostic apparatus according to claim 1, further comprising a fourth storage configured to store an atlas including a plurality of regions into which volume data of the brain segmented, wherein the processing circuitry is further configured to, when a user selects a region from among the plurality of regions included in the atlas, select a region corresponding to the region selected by the user from the regions included in the brain in the image data, and select the region as the target region.

7. A medical imaging apparatus, comprising: the medical image diagnostic apparatus according to claim 1; a setting interface configured to set a first excitation signal for exciting the first scan target region and a first scanning condition with respect to the first scan target region, and set a second excitation signal for exciting the second scan target region and a second scanning condition with respect to the second scan target region; and an imaging system configured to scan the first scan target region based on the first excitation signal and the first scanning condition, and scan the second scan target region based on the second excitation signal and the second scanning condition.

8. A medical imaging apparatus, comprising: processing circuitry configured to obtain image data which is generated by scanning a brain of a subject; select a target region from the image data; extract a connected region of which a brain function is associated with a brain function of the target region, as an additional region, wherein the connected region is a cranial nerve region; and set a first scan target region including the target region to scan the target region in the brain, and set a second scan target region including the additional region to scan the additional region in the brain; a setting interface configured to set a first excitation signal for exciting the first scan target region and a first scanning condition with respect to the first scan target region, and set a second excitation signal for exciting the second scan target region and a second scanning condition with respect to the second scan target region; an imaging system configured to scan the first scan target region based on the first excitation signal and the first scanning condition, and scan the second scan target region based on the second excitation signal and the second scanning condition; and a storage configured to store connection information associating, with respect to each of a plurality of brain functions, a plurality of cranial nerve regions constituting a neural pathway related to a same brain function, wherein the processing circuitry is further configured to identify the brain function of the target region, determine, by referring to the connection information, at least one cranial nerve region constituting a neural pathway related to a brain function that is identical to the brain function of the target region, and extract the at least one cranial nerve region from the image data, as the additional region.

9. A medical imaging method, comprising: obtaining image data which is generated by scanning a brain of a subject; selecting a target region from the image data; extracting a connected region of which a brain function is associated with a brain function of the target region, as an additional region, wherein the connected region is a cranial nerve region; and setting a first scan target region including the target region to scan the target region in the brain, and setting a second scan target region including the additional region to scan the additional region in the brain; storing connection information associating, with respect to each of a plurality of brain functions, a plurality of cranial nerve regions constituting a neural pathway related to a same brain function; identifying the brain function of the target region; determining, by referring to the connection information, at least one cranial nerve region constituting a neural pathway related to a brain function that is identical to the brain function of the target region; and extracting the at least one cranial nerve region from the image data, as the additional region.

10. The method according to claim 9, further comprising: setting one region of the target region and the additional region for one of a right brain and a left brain of the brain of the subject; and setting a third target region including a region corresponding to the one region for the other of the right brain and the left brain for which the one region is not set.

11. The method according to claim 9, further comprising storing the first set scan target region and the second set scan target region in association with subject identification information for identifying the subject.

12. The method according to claim 9, further comprising: storing a plurality of lesion patterns and a plurality of regions of the brain, each lesion pattern of the plurality of lesion patterns being associated with at least one region of the plurality of region of the brain; reading at least one region being associated with a lesion pattern selected by an user from among the plurality of lesion patterns; and selecting the read region as the target region.

13. The method according to claim 9, further comprising: calculating a parameter related to a region of the brain; comparing the parameter with a preset parameter range for the region of the brain; and when the parameter is outside the parameter range, determining the region of the brain as an abnormal region, and select the abnormal region as the target region.

14. The method according to claim 9, further comprising: storing an atlas including a plurality of regions into which volume data of the brain segmented; when a user selects a region from among the plurality of regions included in the atlas, selecting a region corresponding to the region selected by the user from the regions included in the brain in the image data; and selecting the region as the target region.

* * * * *